United States Patent [19]

Cropley

[11] 4,345,104

[45] Aug. 17, 1982

[54] PROCESS FOR THE PRODUCTION OF ETHYLENE GLYCOL

[75] Inventor: Jean B. Cropley, Scott Depot, W. Va.

[73] Assignee: Union Carbide Corporation, Danbury, Conn.

[21] Appl. No.: 278,962

[22] Filed: Jun. 30, 1981

[51] Int. Cl.$^3$ .................. C07C 29/32; C07C 31/20
[52] U.S. Cl. ............................................ 568/852
[58] Field of Search ................................. 568/852

[56] References Cited

PUBLICATIONS

Oyama, "J. Org. Chem.", vol. 30, (Jul. 1965), pp. 2429–2432.

*Primary Examiner*—Joseph E. Evans
*Attorney, Agent, or Firm*—Gary L. Wamer

[57] ABSTRACT

A process for preparing ethylene glycol by the oxidative coupling of methanol in the vapor state.

18 Claims, No Drawings

PROCESS FOR THE PRODUCTION OF ETHYLENE GLYCOL

This invention relates to a new process for the production of ethylene glycol by the oxygen-promoted dehydrogenation and oxidative coupling of methanol in the vapor phase from methanol or methanol-formaldehyde mixtures.

BACKGROUND OF THE INVENTION

The production of ethylene glycol from other than petroleum sources has been long sought. The dire predictions of significant oil shortages in the future, as well as the cost of producing chemicals from petroleum sources, have resulted in the search for a different low cost source which can be converted into the valuable chemical ethylene glycol. Synthesis gas is one such source which can be produced from non-petroleum sources. Synthesis gas is derived by the combustion of carbonaceous materials including coal, or any organic material, such as hydrocarbons, carbohydrates and the like.

Among the chemicals which may be produced from synthesis gas is methanol. Methanol so produced is a valuable starting material for the manufacture of other useful chemicals.

U.S. Pat. No. 2,153,064 discloses a process for preparing ethylene glycol using methanol as the starting material. In this process methanol is first converted to formaldehyde which is then converted to ethylene glycol.

U.S. Pat. No. 2,152,852 discloses a process for reacting formaldehyde, carbon monoxide and water under high pressure with an acid catalyst to produce hydroxyacetic acid. The hydroxyacetic acid was then reacted with methanol to give the methyl ester of ethylene glycol which was converted to ethylene glycol by catalytic hydrogenation.

French Pat. No. 666,681 discloses a process for manufacturing organic products, such as ethylene glycol, by the oxidation under high pressure (between 100 and 800 kilograms) at a temperature not exceeding 500° C. of raw materials, for example, methanol, in a reaction tube. (A second reaction tube is provided too as a safety tube.)

For a review of the synthesis of ethylene glycol by irradiation of methanol, reference should be made to The Radiolysis of Methanol: Product Yields, Rate Constants, and Spectroscopic Parameters of Intermediates, U.S. Department of Commerce/National Bureau of Standards NSRDS-NBS 54,1975.

U.S. Pat. No. 4,076,758 discloses a process for coupling relatively low-molecular weight primary alcohols to form relatively higher molecular weight vicinal glycols employing a trialkylselyl protecting group on the hydroxyl position of the low molecular weight primary alcohol during the coupling reaction. Of particular interest is the recognition at column 2, line 26 et. seq., "That the direct coupling of methanol undesirably leads to a substantial amount of formaldehyde is seen from the work of Schwetlich et al., Angew. Chem. 72, 779 (1960); and Ladygin and Saraeva, Kinetics and Catalysis, 6, 189-95 (1965) and 7, 832-39 (1966)."

SUMMARY OF THE INVENTION

The instant process relates to the preparation of ethylene glycol by the oxidative coupling of methanol in the presence of oxygen at a temperature of between about 450° C. and about 800° C. The process is carried out in two reaction zones such that substantially no oxygen is present in the second reaction zone wherein ethylene glycol is formed.

DETAILED DESCRIPTION OF THE INVENTION

In accordance with the instant invention, ethylene glycol is prepared from the starting material methanol in the presence of molecular oxygen at a temperature between about 450° C. and about 800° C. by the oxidative coupling of methanol. The process is carried out in two reaction zones.

The process of this invention involves the oxidative coupling of methanol using oxygen without over oxidation of methanol to undesirable by-products. The reaction is believed to take place in two distinct reaction zones. The reaction in the first reaction zone involves the use of oxygen to form the hydroxymethyl radical. The reaction in the second reaction zone involves the coupling of hydroxymethyl radicals wherein such coupling reaction is carried out in a substantially oxygen free second reaction zone. Although the process is necessarily carried out in two reaction zones, these reaction zones may in fact be within a single reaction vessel, e.g., the two reaction zones may comprise respective portions of a tube-type or other suitable reactor.

The instant process will be more clearly understood by reference to the following description of the free-radical chemistry believed to be involved:

Free Radical Initiation Step (1) $CH_3 + O_2 \rightarrow CH_2OH + HO_2$ (Slow)

Free Radical Propagation Steps (2) $CH_2OH + O_2 \rightarrow HCHO + HO_2$ (3) $HCHO + O_2 \rightarrow CHO + HO_2$ (4) $HCHO + HO_2 \rightarrow CHO + H_2O_2$ (5) $CHO + O_2 \rightarrow CO + HO_2$ (6) $CH_3OH + HO_2 \rightarrow CH_2OH + H_2O_2$ (primary source of $CH_2OH$)

Free Radical Termination Steps (7) $2CH_2OH \rightarrow (CH_2OH)_2$ (Formation of EG)

(8) $2CH_2OH \rightarrow HCHO + CH_3OH$ (Disproportionation)

(9) $HO_2 + H_2O_2 \rightarrow H_2O + O_2 + HO$

(10) Radical + Surface → Inert

In equation 1, the hydroxymethyl radical is formed by reaction of methanol and oxygen with the additional formation of the $HO_2$ radical which reacts by way of equation 6 in the first reaction zone (radical propagation zone) to form the hydroxymethyl radical. Since the hydroxymethyl radical will oxidize to formaldehyde, as shown in equation 2, it is important to provide the $HO_2$ radicals an opportunity to reaction with methanol in an environment that is essentially oxygen free.

Further, the disproportionation reaction of equation 8 is relatively slow as compared to the coupling reaction when the reaction temperature is below about 400° C. whereas the disproportionation reaction accelerates as the temperature increases. It has been observed that ethylene glycol is not formed in appreciable quantity below about 450° C. and very little ethylene glycol is formed below about 500° C. This is believed to arise from the energy required to oxidatively abstract the carbon-bound hydrogen. Since at the higher temperatures the disproportionation reaction accelerates, it is important to decrease the process temperature when oxygen has been consumed. This will provide for a maximization of ethylene glycol formation. The remaining equations (3, 4, 5, 9, and 10) set forth other free-radical steps believed to occur in the instant process.

The product of equation (7) is ethylene glycol and is, thus, the preferred free radical termination step. In carrying out the process, the temperature is between about 450° C. and about 800° C., preferably between about 500° C. and 700° C. and most preferably between about 550° C. and about 650° C.

The pressure employed in the two reaction zones is preferably between about 0.1 atmosphere and about 20 atmospheres, preferably between about 1 atmosphere and about 10 atmospheres and most preferably between about 1 atmosphere and 5 atmospheres.

The concentration of the process reactants, i.e. methanol and molecular oxygen, is not narrowly critical and may, respectively, vary over wide ranges. The concentration of methanol, as a mole percent based on the total moles present in the reactor feed, is generally between about 10 and about 90 mole percent, preferably between about 20 and about 70 mole percent and most preferably between about 40 and about 60 mole percent. The concentration of molecular oxygen, as a mole percent based on the total moles in the reactor feed, is generally between about 0.5 and about 40 mole percent, preferably between about 2 and about 30 mole percent and most preferably between about 5 and about 10 mole percent.

The process is generally carried out in the presence of an inert gaseous diluent such that the remainder of the process volume comprises the inert gaseous diluent. The inert gaseous diluent may comprise any gas that is inert under the process conditions, such as nitrogen, argon, carbon monoxide carbon dioxide and the like. Nitrogen and carbon dioxide are preferred inert gaseous diluents.

As noted above in equation 8, one of the reaction products of the disproportionation reaction is formaldehyde. It has been discovered that by using a a mixture containing methanol and formaldehyde as the feed for the process, that the ratio of glycol to formaldehyde in the resulting products obtained from the process may be significantly increased. The resulting reaction products contain an increase in the amount of ethylene glycol formed and a decrease in the amount of formaldehyde formed. Thus, formaldehyde (paraformaldehyde) may be employed such that the mole percent formaldehyde, based on the total moles on the reactor feed (total moles of methanol and formaldehyde), is between 0.001 and about 50 mole percent, preferably between 0.1 and about 30 mole percent and most preferably between 0.5 and about 20 mole percent, such that the mole ratio of ethylene glycol to formaldehyde (i.e. formaldehyde formed in the process) increases as compared to when formaldehyde is not provided in a mixture with methanol in the process feed.

The process is carried out in relatively short reaction times (i.e. residence time in the reaction zones) with the reaction time being generally between about 0.01 and about 30 seconds, preferably between about 0.02 and about 10 seconds and most preferably between about 0.1 and about 1.0 second. Although longer or shorter reaction times (residence times) may be employed, the reaction time for the process is typically within the aforementioned ranges.

The process is carried out in two reaction zones, i.e., a first, hydroxymethyl radical-forming zone (radical-forming zone) and a second, hydroxymethyl radical-coupling zone (radical-coupling zone). The two reaction zones may be contained in a single reactor, e.g., a tubular reactor or may be contained in separate reactors. The process is preferably carried out in a reactor formed of a quartz U-tube since a quartz tube is relatively inert reactor material. The actual selection of the reactor material is of importance owing to the free radical reactions involved in the process, since a reactor material which serves to quench the free radicals prior to the radical-coupling zone necessarily reduces the formation of the principle product ethylene glycol and may increase the amount of formaldehyde formed (see equation 10).

In selecting the reactor design to be employed herein, the reactor should be selected so as to preferably have a relatively low surface-to-volume ratio. The surface to volume ratio is preferably between 0.001 to about 1.0 $cm^{-1}$ and more preferably between 0.001 to 0.01 $cm^{-1}$. In general, the lower the surface-to-volume ratio the better is the selectivity and productivity to ethylene glycol. In addition, the reactor design is generally selected to minimize hot-spots which may lead to an increase in the formation of formaldehyde and, accordingly, a decrease in the formation by ethylene glycol.

In carrying out the process, the rate to glycol is typically between about 4 to about 5 gram mole liter$^{-1}$ hr$^{-1}$ of reactor volume. The selectivities are generally between about 12 and 15 percent, based on total methanol converted to product, although selectivities between about 40 and about 50 percent are believed attainable.

The process is carried out such that the radical-coupling zone is substantially oxygen free. The concentration of oxygen in the radical coupling zone is preferably less than about 500 parts per million (ppm), more preferably less than about 100 ppm and most preferably less than about 50 ppm.

In carrying out the process, the temperature/time relationship in the two reaction zones are critical if ethylene glycol is to be formed as is exemplified in the examples hereinafter and as discussed hereinbefore in the discussion of the process conditions.

EXPERIMENTAL PROCEDURE

The examples set forth hereinafter were carried out in a quartz U-tube reactor approximately 20 inches long having an internal diameter of approximately 6 mm. The U-tube, containing both the radical-forming and radical-coupling reaction zones, was heated by placement in a fluidized sand bath wherein air or nitrogen was employed as the fluidizing medium. Heat was supplied to the heating medium by means of electrical resistance heaters submersed in the sand bath. Liquid methanol is introduced by means of a standard laboratory syringe pump to an electric preheater wherein it is vaporized and heated to a temperature of about 200° C. At the outlet of the electric resistance preheater, the vaporized methanol is admixed with a mixture of inert gaseous diluent and oxygen, after which the combined mixture is introduced to the quartz U-tube reactor which is proximately placed in relation to the electric preheater. The quartz U-tube comprises both the radical-forming zone and radical-coupling zone. The quartz U-tube is heated to the process temperature by means of the electrical resistance heaters submersed in the sand bath. The product stream exiting the quartz U-tube reactor passes to a cold water condenser and then to a ice-water-cooled condenser wherein liquid condensate (effluent condensate) is collected. The condensate product is analyzed by gas chromatography (Varian (TM) 3700) using a Chromosorb (TM) 101 column and a time/temperature program. The gases exiting the process (uncondensed effluent) are analyzed as set forth herein for the condensate product except that the column is at a constant temperature.

The following examples are provided to illustrate the invention and are not to be construed as limiting the invention in any way.

EXAMPLE 1

The process of this invention was carried out according to the above-described experimental procedure wherein the temperature of the sand bath was about 600° C. and the temperature of the gaseous mixture at the outlet of the preheater was about 160° C. It was estimated that about two thirds of the quartz U-tube was required for heating the gaseous mixture to the temperature of the sand bath. The process pressure was maintained at about 1 atmosphere. The rate at which the gaseous feed was fed was about 1.914 gram moles hour$^{-1}$ of nitrogen, and 0.208 gram moles hour$^{-1}$ of molecular oxygen, 1.6 grams moles hour$^{-1}$ of methanol, (liquid) and 0.19 gram moles hour$^{-1}$ of paraformaldehyde (liquid). The volume of the quartz U-tube reactor that was employed as the reaction zone (comprising both reaction zones) was estimated to be about 0.0073 liters. The reactor outlet was fed to an ice-water-cooled condenser and liquid condensate (effluent condensate) was collected for analysis by gas chromatography (using a Chromosorb (TM) 101 column as aforementioned). The total time the process was carried out was 30 minutes, after which the productivity to ethylene glycol, formaldehyde (including formaldehyde/water), methyl formate and carbon monoxide were calculated respectively to be 4.42 gram moles liter$^{-1}$ hour$^{-1}$, 15.34 gram moles liter$^{-1}$ hour$^{-1}$, 1.10 gram moles liter$^{-1}$ hour$^{-1}$ and 34.93 gram moles liter$^{-1}$ hour$^{-1}$. The composition of the gaseous mixture at the inlet and outlet of the quartz U-tube reactor is set forth in Table I.

TABLE I

| Compound | Inlet[1] | Outlet[1] | Net[2] |
|---|---|---|---|
| Methanol | 1.60 | 1.13 | (0.47) |
| Oxygen | 0.208 | 0 | (0.208) |
| Nitrogen | 1.914 | 1.914 | 0 |
| Paraformaldehyde | 0.19 | 0 | 0[3] |
| Formaldehyde/Water | 0 | 0.302 | 0.302 |
| Carbon monoxide | 0 | 0.255 | 0.255 |
| Water | 0 | 0.14 | 0.14 |
| Methyl Formate | 0 | 0.008 | 0.008 |
| Ethylene Glycol(EG) | 0 | 0.0323 | 0.0323 |
| Unknowns as | 0 | 0.0105 | 0.0105 |

TABLE I-continued

| Compound | Inlet[1] | Outlet[1] | Net[2] |
|---|---|---|---|
| Ethylene Glycol | | | |

[1]reported in gram moles hour$^{-1}$
[2]a number in parenthesis indicates a net loss
[3]paraformaldehyde measured as formaldehyde/water

EXAMPLE 2

This example was carried out under the conditions set forth in example 1 except that the percent oxygen at the outlet of the quartz U-tube reactor was varied as set forth in Table II. The presence of oxygen in the effluent (outlet) of the U-tube reactor coincided with a lack of detectable ethylene glycol being present in the effluent.

TABLE II

| Time[1] | Oxygen[2] | Ethylene Glycol[3] |
|---|---|---|
| 0 | 0 | 2.75 |
| 15 | 5 | 0 |
| 25 | 0 | 2.95 |

[1]time in minutes
[2]oxygen given as a weight percent based on total effluent weight
[3]ethylene glycol given as a weight percent based on total effluent condensate.

EXAMPLE 3

This example was carried out according to the procedure of example 1 except that the pressure employed was about 15 psig, the gaseous feed mixture was methanol containing 10 percent by weight paraformaldehyde and the inert gaseous diluent was carbon dioxide containing 9.8 percent by weight molecular oxygen. Ethylene glycol was formed at the rate of 4.3 gram moles hour.

EXAMPLE 4

This example demonstrates the effect that formaldehyde as on the rate of formation of ethylene glycol in the instant process.

The process was carried out according to the procedure of example 1 except that the gas feed rate was about 52 liters per hour with carbon dioxide as the inert gaseous diluent containing 9.6 percent oxygen. The liquid feed rate was 72 milliliter per hour and comprised either methanol or ethanol with 10 percent by weight paraformaldehyde which resulted in the quantity of ethylene glycol detected for a fixed time at 2.45 percent by weight and 3.0 percent by weight of the reactor condensate.

EXAMPLE 5

This example was carried out according to the procedure of example 1 except that the methanol feed contained 10 percent by weight paraformaldehyde and the inert gaseous diluent contained 8.4 percent by weight molecular oxygen. This example demonstrates the effect of surface degradation after employment of a given reactor surface for an extended period of time. Table III sets forth the results and conditions of this example.

TABLE III

| Time[1] | Temperature(°C.) | Liquid Feed Rate[3] | Gas[4] Feed Rate | Ethylene[5] Glycol |
|---|---|---|---|---|
| 0 | 600 | 36 | 45 | 2.4 |

TABLE III-continued

| Time[1] | Temperature(°C.) | Liquid Feed Rate[3] | Gas[4] Feed Rate | Ethylene[5] Glycol |
|---|---|---|---|---|
| 331[2] | 600 | 36 | 42 | 0.25 |

[1]time in hours
[2]the actual time was 330 hours and 58 minutes. The reactor did not undergo continuous operation over the time but instead was intermittently operated.
[3]rate given in milliliter hour$^{-1}$
[4]given in liters hour$^{-1}$
[5]ethylene glycol given as a weight percent of the effluent condensate.

EXAMPLE 6

This example demonstrates the effect of increasing the quartz surface such that the surface-to-volume ratio is increased, i.e. the overall void volume is decreased. To demonstrate the effect of employing an increased surface-to-volume ratio the experimental procedure according to example 1 was employed except that the quartz U-tube was packed with quartz chips, as noted. The results of this example are set forth in Table IV wherein three runs (A,B and C) and process conditions are given.

TABLE IV

| Run | Temperature (°C.) | Oxygen[3] | Ethylene Glycol[4] |
|---|---|---|---|
| A[1] | 600 | 0 | 2.1 |
| B[2] | 650 | 0 | 0.6 |
| C[2] | 600 | 7.0 | 0.1 |

[1]no quartz chips were employed.
[2]quartz chips were employed
[3]oxygen present in the effluent from quartz U-tube reactors given as a weight percent
[4]ethylene glycol present in the effluent condensate from quartz U-tube reactor given as a weight percent of the condensate.

EXAMPLE 7

The experimental procedure of Example 1 was repeated except that the quartz U-tube was replaced by a straight quartz tube reactor about ⅝ inch in length, surmounted by a 3 inch quartz tube. The internal diameter of the reactor was approximately 6 millimeters. The inert gaseous diluent was carbon dioxide containing 7.4 percent oxygen. The reaction temperature was about 610° C., the liquid feed rate was 72 milliliter hour$^{-1}$ and the gaseous feed rate was about 108 liter hour$^{-1}$.

After carrying out the process for a given period of time the liquid condensate from the reactor effluent contained 3.3 percent by weight ethylene glycol.

EXAMPLE 8

To demonstrate the effect of reactor "back-mixing" on the process the experimental procedure of example 1 was repeated except that the quartz U-tube reactor was modified to provide a relatively cool incoming gas to be passed over the surface of the quartz U-tube thereby minimizing the effects arising from the surface characteristics of the reactor. The reactor was operated in a back-mixed flow regime by use of a conical mixing chamber with tangential introduction of the feed, using reactor tube which was a capillary tube having a 1 millimeter internal diameter.

A rate to ethylene glycol of about 0.015 gram moles hour$^{-1}$ was observed which corresponds to about fifty percent of the rate observed in Example 1, supra.

EXAMPLE 9

The process was carried out according to the procedure of example 1, except that the inert gaseous diluent nitrogen contained 8.4 percent by weight oxygen and methanol containing 10 percent by weight paraformaldehyde was employed and the temperature was alternatively 600° C., 400°., and 350°. The effect on the production of ethylene glycol with decreasing temperature is set forth in Table V wherein the results of this Example are given.

EXAMPLE V

| Liquid Feed Rate[1] | Gas Feed Rate[2] | Temperature (°C.) | Ethylene[3] Glycol |
|---|---|---|---|
| 18 | 24 | 600 | 1.4 |
| 15 | 24 | 400 | 0.10 |
| 15 | 24 | 350 | 0.00 |

[1]liquid feed rate of methanol/paraformaldehyde mixture in milliliter hour$^{-1}$
[2]gas feed rate of nitrogen/oxygen mixture in liters hour$^{-1}$
[3]ethylene glycol produced as a weight percent of the effluent condensate

What is claimed is:

1. A process for the production of ethylene glycol by the oxidative coupling of methanol in the vapor state wherein said process comprises:
   (1a) introducing methanol and oxygen into a first reaction zone at a temperature sufficient to form hydroxymethyl radicals in the vapor state and;
   (1b) introducing the hydroxymethyl radicals into a reaction zone wherein said oxidative coupling occurs at a temperature between about 450° C. and 800° C. in the vapor state, said second reaction zone being substantially oxygen free.
2. The process of claim 1 wherein the temperature in (a) is between about 450° C. to about 800° C.
3. The process of claim 2 wherein the temperature in steps (a) and (b) is between about 500° C. and about 700° C.
4. The process of claim 3 wherein the temperature in steps (a) and (b) is between about 550° C. and about 650° C.
5. The process of claim 1 wherein the concentration of oxygen in the second reaction zone is less than about 500 ppm.
6. The process of claim 5 wherein the concentration of oxygen is less than about 100 ppm.
7. The process of claim 1 wherein said process is carried out at a pressure between about 1 atm and 10 atm.
8. The process of claim 7 wherein said process is carried out between about 1 atm and 5 atm.
9. The process of claim 1 wherein the reaction time in each reaction zone is between about 0.01 to 30 seconds.
10. The process of claim 9 wherein the reaction time in each reaction zone is between about 0.02 and 10 seconds.
11. The process of claim 1 wherein the process is carried out in the presence of an inert gaseous diluent.
12. The process of claim 11 wherein the inert gaseous diluent is nitrogen.
13. The process of claim 11 wherein the inert gaseous diluent is carbon dioxide.
14. The process of claim 1 wherein the ratio of reactor surface area to the reactor volume is between about 0.001 to 1.0 cm$^{-1}$.
15. The process of claim 1 wherein formaldehyde is added in sufficient concentration to increase the production of ethylene glycol.
16. The process of claim 15 wherein the concentration of formaldehyde is between about 0.001 and 50 mole percent.
17. The process of claim 16 wherein the concentration of formaldehyde is between about 0.1 and about 30 mole percent.
18. The process of claim 17 wherein the concentration of formaldehyde is between about 0.5 and about 20 mole percent.

* * * * *